US006248938B1

(12) United States Patent
Austin-Phillips et al.

(10) Patent No.: US 6,248,938 B1
(45) Date of Patent: Jun. 19, 2001

(54) ANIMAL FEED COMPOSITIONS CONTAINING PHYTASE DERIVED FROM TRANSGENIC ALFALFA AND METHODS OF USE THEREOF

(75) Inventors: Sandra Austin-Phillips; Richard G. Koegel, both of Madison; Richard J. Straub, Brooklyn; Mark Cook, Madison, all of WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/241,275

(22) Filed: Feb. 1, 1999

Related U.S. Application Data (60) Division of application No. 08/807,370, filed on Feb. 27, 1997, now Pat. No. 5,900,525, which is a continuation-in-part of application No. 08/638,448, filed on Apr. 26, 1996, now Pat. No. 5,824,779.

(51) Int. Cl.[7] .............................. A01H 5/00; A01H 1/00; A01H 11/00; G01N 33/20
(52) U.S. Cl. ..................... 800/298; 800/288; 800/295; 800/278; 436/74; 436/615; 436/623
(58) Field of Search .................................. 800/288, 278, 800/295, 298; 436/74, 615, 623

(56) References Cited

U.S. PATENT DOCUMENTS

| | | | |
|---|---|---|---|
| 2,600,903 | 6/1952 | Miller . | |
| 5,436,156 | 7/1995 | Van Gorcom et al. | 435/252.3 |
| 5,593,963 | 1/1997 | Van Ooijen et al. | 514/12 |
| 5,824,779 | * 10/1998 | Koegel et al. | 530/370 |

OTHER PUBLICATIONS

Austin et al. (1994), An overview of a feasibility study for the production of industrial enzymes in transgenic alfalfa, Annals N.Y. Acad. of Sci., (721):234–242.
Austin et al. (1995), Euphytica, 00:1–13.
Ehrlich et al. (1993), Biochem. & Biophys. Res. Comm., 195(1): 53–57.
Gibson, D.M. and Ullah, A.B.J.
(1990), Inositol metabolism in plants, Wiley–LISS, Inc., 77–82.
Han et al. (1995), Proceedings of the 1995 Cornell Nutrition Conference for Feed Manufacturers, Rochester, New York, pp. 149–152.
Hughes, G.P. and Eyles, D.E. (1952), Extracted Herbage Leaf Protein for Poultry Feeding, J. Agric. Sci (Cambridge), 43:136–143.
Knuckles et al. (1975), Soluble protein from alfalfa juice by membrane filtration, J. Agric. Food Chem., 23(2):209–212.
Knuckles and Kohler (1982), Functional Properties of Edible Protein Concentrates From Alfalfa, J. Agric. Food Chem., 30:748–752.
Koganov et al. (1988), The Influence of Alternating Electric Current on Alfalfa Chloroplast Coagulation (Original in russian), Phys. and Biochem. of Cultural Plants, 20(2):195–200.
Kohler et al. (1983), LPC for Feed and Foods: The ProXan Process, Telek and Graham, eds., "Leaf Protein Concentrates," AVI Publ. Co., pp. 508–24.
Ostrowski–Meissner, H.T. (1983), Protein concentrates from pasture herbage and their fractionation into feed– and food––grade products, Telek and Graham, eds., "Leaf Protein Concentrates," AVI Publ. Co., pp. 437–66.
Verwoerd et al. (1995), Plant Physiology, 109:1199–1205.

\* cited by examiner

*Primary Examiner*—Jeffrey Fredman
*Assistant Examiner*—Juliet C. Einsmann
(74) *Attorney, Agent, or Firm*—Joseph T. Leone, Esq.; DeWitt Ross & Stevens S.C.

(57) ABSTRACT

A value-added composition of matter containing plant matter from transgenic alfalfa which expresses exogenous phytase activity is disclosed. The phytase activity is a gene product of an exogenous gene encoding for phytase which has been stably incorporated into the genome of alfalfa plants. The transgenic alfalfa expresses phytase activity in nutritionally-significant amounts, thereby enabling its use in animal feeds to eliminate the need for phosphorous supplementation of livestock, poultry, and fish feed rations.

9 Claims, 4 Drawing Sheets

ANIMAL FEED COMPOSITIONS CONTAINING PHYTASE DERIVED FROM TRANSGENIC ALFALFA AND METHODS OF USE THEREOF

This is a Divisional of co-pending application Ser. No. 08/807,370 filed Feb. 27, 1997; which is a Continuation-In-Part of application Ser. No. 08/638,448 now U.S. Pat. No. 5,900,525, filed Apr. 26, 1996 now U.S. Pat. No. 5,824,779.

This invention was made with United States government support awarded by the following agencies:

DOE Grant # DE-FG05-920R22072; DOE Grant # OR22072-14; USDA Grant # 92-34190-6941; USDA Grant # 95-34340-1605; USDA AGRICARS Grant # 58-3655-6-132; USDA AGRICCREE Grant # 94-33120-0433, Hatch Grant #3194, N194; and USDA AGRICARS Grant # 58-3655-2-205, 58-3655-7-208.

The United States has certain rights in this invention.

FIELD OF THE INVENTION

The invention is drawn to value-added animal feed compositions and additives containing unprocessed or minimally processed matter from transgenic alfalfa which expresses exogenous phytase activity in concentrations nutritionally significant in monogastric animals. The invention is further drawn to novel uses of the animal feed compositions.

BIBLIOGRAPHY

Complete bibliographic citations of the references described herein can be found in the Bibliography section, immediately preceding the claims.

DESCRIPTION OF THE PRIOR ART

Livestock production, especially large-scale commercial livestock production for human consumption, requires the use of vast amounts of nutritionally balanced animal feed. Because of the large amounts of feed required to sustain commercial livestock production, world-wide research efforts have been made to develop feedstock additives which maximize the bioavailability of nutritionally important elements and compounds found in common animal feedstocks.

In the early 1950's, for instance, it was speculated that the dietary requirements of egg-laying fowl might be met by utilizing protein-rich extracts from green plants. Hughes and Eyles (1953) describe a feeding trial with laying hens which used dietary protein extracted from the leaves of green plants. The authors hypothesized that dietary protein could be extracted from green plants in an economical fashion, thereby easing the shortage and lowering the cost of high protein feed in Great Britain.

In more recent years, with the development of sophisticated methods of genetic manipulation, transgenic plants which express nutritionally important compounds have been developed. However, in order to effectively utilize transgenic plants which express exogenous proteins, the transgenic plants must be more economical to use than the feedstocks or feedstock additives they are designed to replace.

Therefore, it is necessary to maximize the expression of the exogenous protein while simultaneously stabilizing the beneficial activity of the protein. Additionally, the exogenous expressed protein ideally should be utilizable with very little or no post-harvest processing of the transgenic plant material. If the exogenous protein is expressed in only small quantities, or if the transgenic plant material must be extensively processed prior to use, or if the exogenous protein lacks sufficient stability in the harvested plant material, the slim profit margins encountered in commercial feed production will dictate against switching to the use of transgenic plant material. In short, because alternative sources of nutrients continue to be relatively cheap and widely available, the positive economics of producing nutritionally important feed additives in transgenic plants remains marginal unless the above criteria are present.

The remarkable progress in recombinant plant genetics has greatly spurred new investigations into the economics of manufacturing, isolating, and using exogenous proteins expressed in transgenic herbage plants such as alfalfa. In effect, valuable recombinant protein products, which are now produced by fermentation using transgenic microorganisms, might be economically produced using transgenic plants rather than native or recombinant microbes.

Austin et. al. (1994) studied the production of industrial enzymes in transgenic alfalfa, a report of which appeared in the *Annals of the New York Academy of Sciences*. These investigators researched the feasibility of producing industrially important enzymes using alfalfa plants as "factories." The focus of this study was whether, using genetic engineering technology, cloned genes for valuable enzymes could be expressed and economically harvested from plant hosts. The concept is economically attractive because, assuming the heterologous gene can be stably incorporated, many herbage plants are perennial, hardy crops, which are capable of more than one harvest per year. In the case of alfalfa specifically, in temperate climates such as those found in the midwestern United States, alfalfa does not require irrigation and is capable of three or more harvests a year. Moreover, since alfalfa is leguminous, it grows well without nitrogen fertilizer.

The Austin et al. paper noted above used a reporter gene, β-glucuronidase (GUS), as a model system. The analysis concluded (as noted generally above) that the concentration of the desired value-added product (in this case, GUS) in the transgenic plant is most critical variable for economic viability. Analogous field studies for transgenic alfalfa which expresses α-amylase and manganese-dependent lignin peroxidase have also been reported by Austin et al. (1995).

An enzyme group of particular interest is the phytases. Phytases, more properly referred to as myo-inositol hexaphosphate phosphohydrolases, are a family of enzymes which catalyze the step-wise removal of inorganic orthophosphate from phytic acid (myo-inositol 1,2,3,4,5,6-hexakisphosphate). The economic interest in phytase is due to its ability to increase the bio-availability of inorganic phosphorous in phytate-containing non-ruminant animal feeds. Currently, feed for non-ruminant animals must be supplemented with inorganic phosphorous because these animal cannot utilize the phosphorous present as phytate.

While phytase occurs widely in both plants and microorganisms, the enzyme has been extensively studied mostly from the filamentous fungi, particularly the Aspergilli, notably *A. ficuum*, and *A. nidulans*. For an excellent review of phytases and their action on phytic acid see Gibson, D. M. and Ullah, A. B. J. (1990), incorporated herein by reference.

Regarding the nucleotide sequences which encode phytase, several such sequences have been identified, sequenced, and cloned into various heterologous hosts. For instance, Van Gorcom et al., U.S. Pat. No. 5,436,156, incorporated herein by reference in its entirety, describe the isolation and cloning from *A. ficuum* of a DNA sequence coding for phytase. The isolated nucleotide sequence was successfully cloned and inserted into a vector capable of transforming a microbial expression host. Specifically, the nucleotide sequence was first cloned using the bacteriophage lambda AFD01, and further sub-cloned into pAN 8-1 and pUC19. The construct was then used to transform various types of filamentous fungi. (See also, EP 0 420 358 A1, to the same inventor.)

Ehrlich et al. (1993), describe the cloning and sequencing of a gene for a second type of phytase, designated PhyB. This phytase was isolated from *A. niger* NRRL 3135, and had a pH optimum of 2.5. PhyB was found to have different properties from the previously known phytase PhyA, which has a pH optimum of 5.0.

European Patent Application EP 0 449 375 A2 (Pen et al.) describes the expression of phytase in tobacco seeds and rapeseeds.

Likewise, Verwoerd et al. (1995) describe the production and accumulation of phytase in the leaves of tobacco plants transformed with a phytase-coding gene of *A. niger*. This paper describes the constitutive expression of a phytase cDNA from transgenic tobacco plants. The exogenous phytase enzyme was secreted into the extracellular fluid at concentrations approximately 90 times higher than that in the total leaf extract. The phytase produced by the transgenic tobacco plants was compared to native Aspergillus phytase and found to have identical activities. During plant maturation, it was found that the phytase produced in the tobacco remained biologically active and accumulated in amounts up to 14.4% of the total soluble protein found in the tobacco.

As noted briefly, above, the economic interest in phytase is due to its ability to increase the bio-availability of inorganic phosphorous in phytate-containing animal feeds. The increase in intensive, large-scale livestock production has resulted in increased environmental problems, specifically eutrophication, due to the tremendous amount of manure produced in such enterprises. Phosphorous, an essential nutrient for both ruminants and non-ruminants, is necessarily added to the basal feed provided to livestock. Much of this feed material also contains large amounts of phytate. Phytate acts as the primary storage form of phosphorous in most green plant materials and can account for more than 50% of the total phosphorous content of the plant material. However, in monogastric animals, the phosphorous contained in phytate is poorly digested and largely excreted. Consequently, animal feeds are regularly supplemented with more easily assimilated forms of inorganic phosphorous (e.g., dicalcium phosphate). The excreted phytate, which contains large amounts of phosphorous, increases phosphorous loading to the environment, with concomitant environmental degradation.

Additionally, phytate is generally considered an anti-nutritional factor due to its ability to chelate multivalent cations. For instance, phytate will bind multivalent cations such as calcium, iron, manganese, and zinc, to form insoluble complexes. This reduces the bio-availability of these minerals, which are essential for proper growth and maturation. Further still, phytate also complexes with several different types of proteins, thereby obstructing enzymatic protein digestion.

As a consequence, several prior art references describe the use of phytase-containing compositions to increase the bio-availability of the phosphate contained in phytate.

For instance, European Patent Application EP 0 619 369 A1 (Vanderbeke et al.) describes a phytase-containing enzyme composition which remains enzymatically active at the low pH's found in the digestive tract of monogastric animals. This composition contains a combination of phytases and fungal acid phosphatases. The combination results in a synergistic effect which enables the mixture to enzymatically degrade phytate at relatively low pH. (See also, U.S. Pat. No. 5,443,979, to the same inventors.)

In a study reported in the *Proceedings* of the 1995 Cornell Nutrition Conference for Feed Manufacturers, in Rochester, New York, Han et al. reported that corn-soybean meal diets supplemented with microbial phytase significantly improved the utilization of phosphorous from such feeds and also decreased the amount of phosphorous excreted from swine by up to 50%. These researchers concluded that the need for inorganic phosphorous supplementation in swine feed stocks can be partially or totally eliminated by the addition of dietary microbial phytase during the growth and finishing phase of the swine. It should also be noted however, that the long term effects of phytase supplementation, if any, remain unknown.

Therefore, there remains a need for an affordable, renewable animal feed supplement which enables livestock to more efficiently utilize inorganic phosphorous.

SUMMARY OF THE INVENTION

A first embodiment of the invention is an animal or fish feed composition comprising juice, concentrated juice, or dried juice of transgenic alfalfa plants which constituitively express exogenous phytase activity at a concentration which is nutritionally significant in animals and fish in general, and monogastric animals in particular.

A second embodiment of the invention is an animal or fish feed composition comprising leafy plant material from transgenic alfalfa plants which constituitively express exogenous phytase activity at a concentration which is nutritionally significant in animals, particularly monogastric animals.

A third embodiment of the invention is a feed composition which includes whole non-transgenic alfalfa juice or leafy material from non-transgenic alfalfa to supply xanthophylls, dietary protein and other nutrients to the ration, in combination with whole alfalfa juice, concentrated alfalfa juice, partially fractionated alfalfa juice, or leafy plant material from transgenic alfalfa which expresses phytase activity to supply phytase to the ration. The soluble portion of partially fractionated juice from the transformed plants contains essentially all of the phytase produced in the transformants.

Another embodiment of the invention is drawn to a feed composition for non-fowl, monogastric livestock (swine in particular) which contains partially fractionated juice (as a fresh liquid, frozen, concentrated, or dried) from transgenic alfalfa which expresses phytase activity. Here, the partial fractionation serves to remove xanthopylls from the juice. This is the preferred form of feed for non-fowl livestock because xanthophyll supplementation is not necessary.

A still further embodiment of the invention is a method of feeding livestock, poultry, or fish, in which one of the animal feeds described herein which contains leafy plant material or juice from transgenic alfalfa is fed to livestock, poultry, or fish whereby the need to supplement the feed with inorganic phosphorous is reduced or eliminated entirely.

The value-added feed composition of the present invention is particularly advantageous when added to non-ruminant animal feed. The invention allows non-ruminant animals to utilize phosphorous in the feed more efficiently, thus greatly reducing or eliminating the need for phosphorous supplementation. In addition, use of the feed composition reduces phosphorous loading to the environment, thereby reducing environmental contamination.

Another notable advantage of the disclosed composition is its use in poultry feed. Because the composition contains high levels of pigments such as xanthophylls, and high levels of phytase, poultry feed which is supplemented with the feed composition need not be supplemented with phosphorous or pigmenting agents.

Another distinct advantage of the composition is that it is a value-added product as compared to the market value of the herbage matter of non-transformed alfalfa. This allows farmers and feed formulators to not only diversify their market offerings, but also to increase gross profit margins on otherwise fungible commodity goods.

The principal aim of the invention is to provide a value-added multi-component protein concentrate feed additive from transgenic alfalfa which expresses exogenous phytase. The multi-component composition contains phytase produced by the transgenic alfalfa, pigments such as xanthophylls, and dietary protein.

A still further aim of the present invention is to provide a supplement for monogastric feed rations which can be prepared directly from alfalfa plant matter and which contains high levels of phytase, xanthophylls, and dietary protein.

Further aims, objects, and advantages of the above-described multi-component value-added composition will become apparent upon a complete reading of the Detailed Description, drawings, and attached claims, below.

DETAILED DESCRIPTION OF THE INVENTION

Transgenic Alfalfa Expressing Phytase:

An overriding motivation behind this invention is the use of common agricultural plants which have been genetically engineered to function as "enzyme factories." The use of common, albeit genetically engineered, plants in this fashion significantly impacts the economics of agricultural production. In the case of transgenic alfalfa (the preferred plant host) which expresses exogenous phytase, the invention allows farmers to more effectively feed their non-ruminant livestock at reduced prices, and also reduces phosphorous loading to the environment. Additionally, the plant matter containing the phytase, as well as value-added concentrates and isolates manufactured from the plant material, can be sold at a greater profit than non-transformed herbage matter.

In the present invention, transgenic alfalfa which expresses nutritionally-significant amounts of phytase activity is the preferred plant material. However, any suitably transformed plant species which expresses sufficient levels of phytase and which will not adversely affect livestock by any other mechanism will function with comparable success. Alfalfa is the preferred plant host because alfalfa is a hardy, perennial plant, which grows well with minimal fertilization and irrigation. Alfalfa is also a very prolific plant. In temperate areas such as those found in the mid-western United States, alfalfa will yield three or more harvests per growing season.

Preferably, the alfalfa is stably transformed to constituitively express high levels of enzymatically active phytase. Phytase enzymes are produced in relatively large quantities by many microorganisms, most notably filamentous fungi of the genus Aspergillus. Phytase is also produced by bacteria such as *Bacillus subtilis,* yeasts such as *Saccharonyces cerevisiae,* and various strains of Pseudomonas. Among the filamentous fungi, *Aspergillus ficuum* (*A. ficuum*) produces a phytase which has a particularly high specific activity and thermostability. Phytase of high specific activity is also produced by *A. nidulans* and *A. niger.* In the present invention, it is preferred that the alfalfa plant host be transformed with one or more genetic elements which encode functional phytase, and that the genetic elements originate from a filamentous fungi selected from the group consisting of *A. ficuum, A. nidulans,* and *A. niger.*

The translocated genes may also include upstream or downstream regulatory elements, such as promoters for constituitive, growth stage-specific, or organ-specific expression, targeting sequences, secretory sequences, terminator sequences, polyadenylation signals, and the like, which might function to control gene expression in the heterologous host plant. Such regulatory elements may be homologous (native) to the host plant or they may be heterologous. Several of these types of regulatory sequences are known to those skilled in the art of recombinant plant genetics.

An illustrative method for producing transgenic plants, commonly referred to as the binary vector method, utilizes a strain of Agrobacterium containing a vir plasmid (which includes genes for virulence) and a second, compatible plasmid which contains the gene construct to be translocated.

Here, a double-stranded cDNA encoding phytase is prepared from mRNA isolated from a filamentous fungi of the genus Aspergillus, preferably *A. niger.* For expression in seeds, the DNA construct can be linked with regulatory sequences from the gene encoding the 12S storage protein cruciferin from *Brassica napus.* The construct is then sub-cloned into a binary vector such as pMOG23 (*E. coli.* K-12 strain DH5tα, Centraal Bureau voor Schimmelcultures, Baarn, The Netherlands, Accession No. CBS 102.90). The vector is then introduced into *Agrobacterium tumefaciens* containing a disarmed Ti plasmid. This can be done by any number of well known means, such as by electroporation. Bacterial cells containing the construct are co-cultivated with tissues from alfalfa or other plant to be transformed, and transformed plant cells are selected using nutrient media containing antibiotics. The transformed cells are induced to differentiate into plants on suitable nutrient media. The plants so produced will produce seeds which contain and express the gene construct.

To produce plants which constituitively express the phytase gene construct, the phytase-encoding gene construct is preferably placed under the regulatory control of the 35S promotor sequence of the cauliflower mosaic virus (CaMV). The construct is then sub-cloned into a binary vector as described above. The vector is then introduced into *Agrobacterium tumefaciens* containing a disarmed Ti plasmid. Bacterial cells containing the construct are co-ultivated with tissues from the alfalfa to be transformed, and transformed plant cells are selected using nutrient media containing antibiotics. The transformed cells are induced to differentiate into plants on suitable nutrient media. The plants so produced constituitively express enzymatically active phytase.

The above method is illustrative only, and several other genetic engineering techniques which result in stable transgenic plants will function with equal success in the present invention. As noted above, several such methods are well known in the genetic engineering art. The method by which the transgenic plant starting material is constructed is not critical for the performance of the present invention insofar as the resultant transgenic alfalfa expresses a relatively large amount of functional exogenous gene product.

Figure 4A:
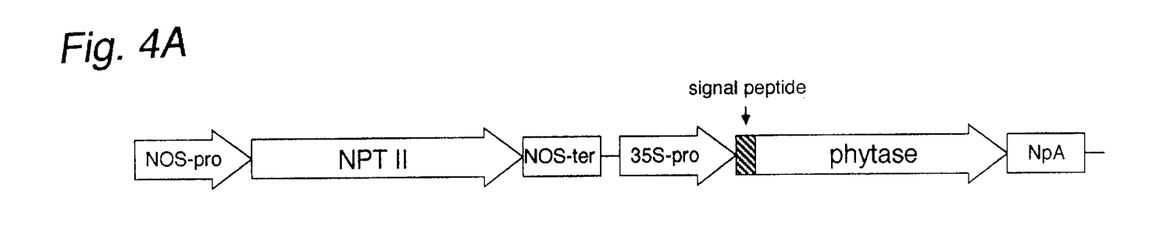
FIGS. 4A, 4B, and 4C are schematic diagrams of the binary vector tDNA of the phytase expression constructs used to transform alfalfa as described herein below. The promoters and structural genes are depicted as arrows which indicate the direction of transcription. Terminaters are depicted as boxes. NOS=nopaline synthase; NPT II=neomycin phosphotransferase; SSU=*Arabidopsis thaliana* Rubisco small subunit promoter; TML=tumor morphology left; 35S=cauliflower mosaic virus 35S promoter.
Figure 4B:
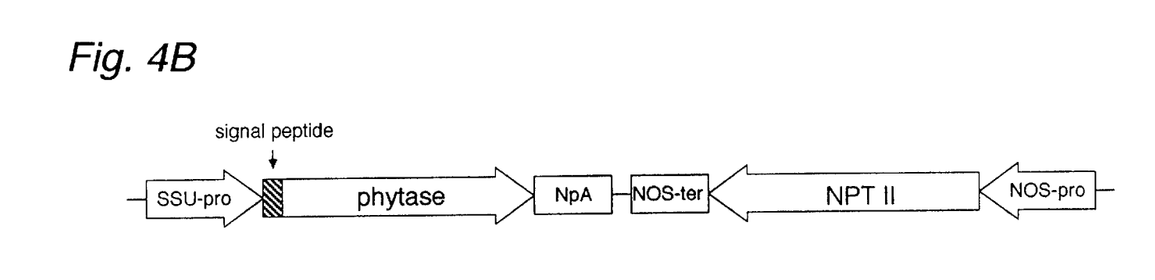
Figure 4C:
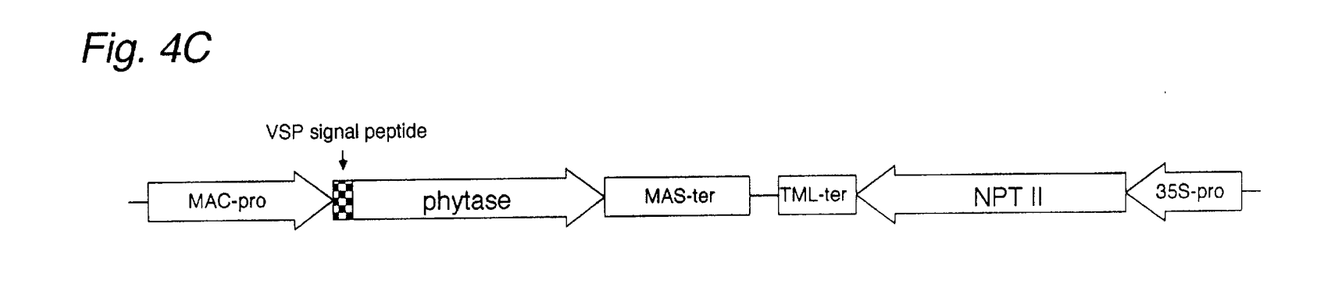

For instance, in the present invention, the preferred transgenic alfalfa was produced as follows: Binary vectors carrying phytase expression cassettes were transformed into *Agrobacterium tumefaciens* strain LBA4404, facilitating Agrobacterium-meditated transformation of plant tissue. The three constructs used are depicted in FIGS. 4A, 4B, and 4C. The constructs shown in FIGS. 4A and 4B contain the *A. niger* phytase gene placed under the control of the CaMV 35S promoter (FIG. 4A) or the *Arabidopsis thaliana* Rubisco small subunit (SSU) promoter (FIG. 4B). The constructs of FIGS. 4A and 4B incorporate a signal peptide for targeting the phytase enzyme to the apoplast. The expression cassettes were cloned into derivative of the pBI binary vectors and mobilized into Agrobacterium.

A third construct, depicted schematically in FIG. 4C, was fabricated in which the hybrid "MAC" promoter was used (pTZ117). This promoter contains distal elements of the CaMV 35S promoter, including the transcriptional enhancer (−940 to −90, relative to the mRNA start site). The proximal promoter elements of MAC are derived from the Agrobacterium mannopine synthase promoter (−301 to +65 relative to the mRNA start site). MAC has been reported to result in higher levels of expression than either of the natural promoters. (See Comai et al. (1990).) The MAC promoter was fused to the *A. niger* phytase gene, along with a signal peptide for apoplast localization as in the first two contructs. This expression cassette was cloned in a pCGN binary vector and mobilized into Agrobacterium.

In vitro transformation of both tobacco and alfalfa was accomplished with all three constructs. Significant levels of phytase expression were obtained in all cases. The phytase expressed appeared underglycosylated in both alfalfa and tobacco, but the enzyme retained stability at high temperature (55° C.) and low pH (pH 2.5).

In transgenic alfalfa, the transformants containing the CaMV 35S promoter gave the best levels of phytase production. Phytase expression in these transformants yielded phytase concentrations ranging from between about 0.1% to about 2.0% of total soluble protein found in the transformed plants. Extensive testing of transformed alfalfa using standardized assays for phytase activity indicated that the transformants expressed phytase constituitively; in all transformants, increased phytase activity was detected throughout the entire plant.

Juicing the Alfalfa:

In order to reduce the amount of material to be handled, phytase present in the transgenic alfalfa may be concentrated by wet fractionation of the freshly harvested alfalfa. Here, the transgenic plant material is harvested, macerated, and fractionated by known means. If further clarification is desired, the juice may be heated by passing alternating current (AC) electricity through the juice or by other means of uniform heat additional. This causes aggregation of insoluble protein particles within the juice, which ten removed from the remaining soluble proteins (which solubles include the exogenous phytase activity). If desired, the phytase within the soluble fraction may be further concentrated by suitable means, such as ultrafiltration, dialysis, and the like.

If the juice of the transgenic alfalfa is to be utilized, the following protocol is preferred. The juice is preferably made from alfalfa in the late bud or early bloom stage. Juicing the alfalfa preferably occurs as soon as practicable after harvesting. It is preferred that the alfalfa be expressed as soon as possible after plant harvest. More preferable still is that the alfalfa be expressed less than 1 hour after plant harvest.

For small batches of juice (up to approximately 15 liters), the alfalfa is first macerated in any suitable type of mechanical macerator, such as an impact macerator. The juice is then immediately expressed using any type of suitable means for pressing. For small batches, a hand-powered hydraulic basket press or screw press is suitable. For larger volumes of plant material, industrial-sized power equipment is required. Any fiber or debris is removed by filtration.

Replacement of Supplemental Phosphate with Juice from Transgenic Alfalfa Expressing Phytase Activity As illustrated in the Examples below, the present inventors have shown that when supplemental phosphate is removed from a basal chicken diet, the chicks quickly develop severe clinical signs of phosphorous deficiency within the first week of life. Chicks which were fed a diet supplemented with alfalfa juice from non-transformed alfalfa also developed severe clinical signs of phosphorous deficiency. However, chicks fed an identical basal diet supplemented with alfalfa juice from transformed alfalfa which expresses phytase activity thrived. This clearly illustrates that the added alfalfa juice, which contains phytase activity, increases the bio-availability of phosphorous present in phytate in the basal diet to the point that supplementation of the ration with inorganic phosphorous is no longer necessary.

Feed Composition Containing Transgenic Alfalfa

In light of the above finding, one aspect of the present invention is a monogastric animal feed ration which includes dry plant matter or juice from transgenic alfalfa which expresses exogenous phytase. The feed ration may contain dried transgenic alfalfa per se, whole juice extracted from the transgenic alfalfa, frozen juice extracted from the transgenic alfalfa, concentrated juice extracted from the transgenic alfalfa, or fractionated portions of the alfalfa juice. The alfalfa per se, or the alfalfa juice or concentrated juice can be added to standard monogastric feed rations, such as the poultry ration described in Example 4 below. Preferably, the transgenic alfalfa or the juice of the transgenic alfalfa is added in quantities sufficient to eliminate the need to supplement the base ration with inorganic phosphorous.

The feed composition may also include leafy plant material or juice from non-transformed alfalfa as well. This is particularly applicable to fowl rations, which conventionally include xanthophyll supplementation to promote good skin and egg yolk coloration. The desired xanthophyll supplementation (as well as additional dietary protein) can be incorporated into the ration by adding non-transformed alfalfa or alfalfa juice to the feed, or by adding xanthophyll extracted from juice products where pigmenting is not desired.

Stability of the Phytase Enzyme from Transgenic Alfalfa

Figure 2:
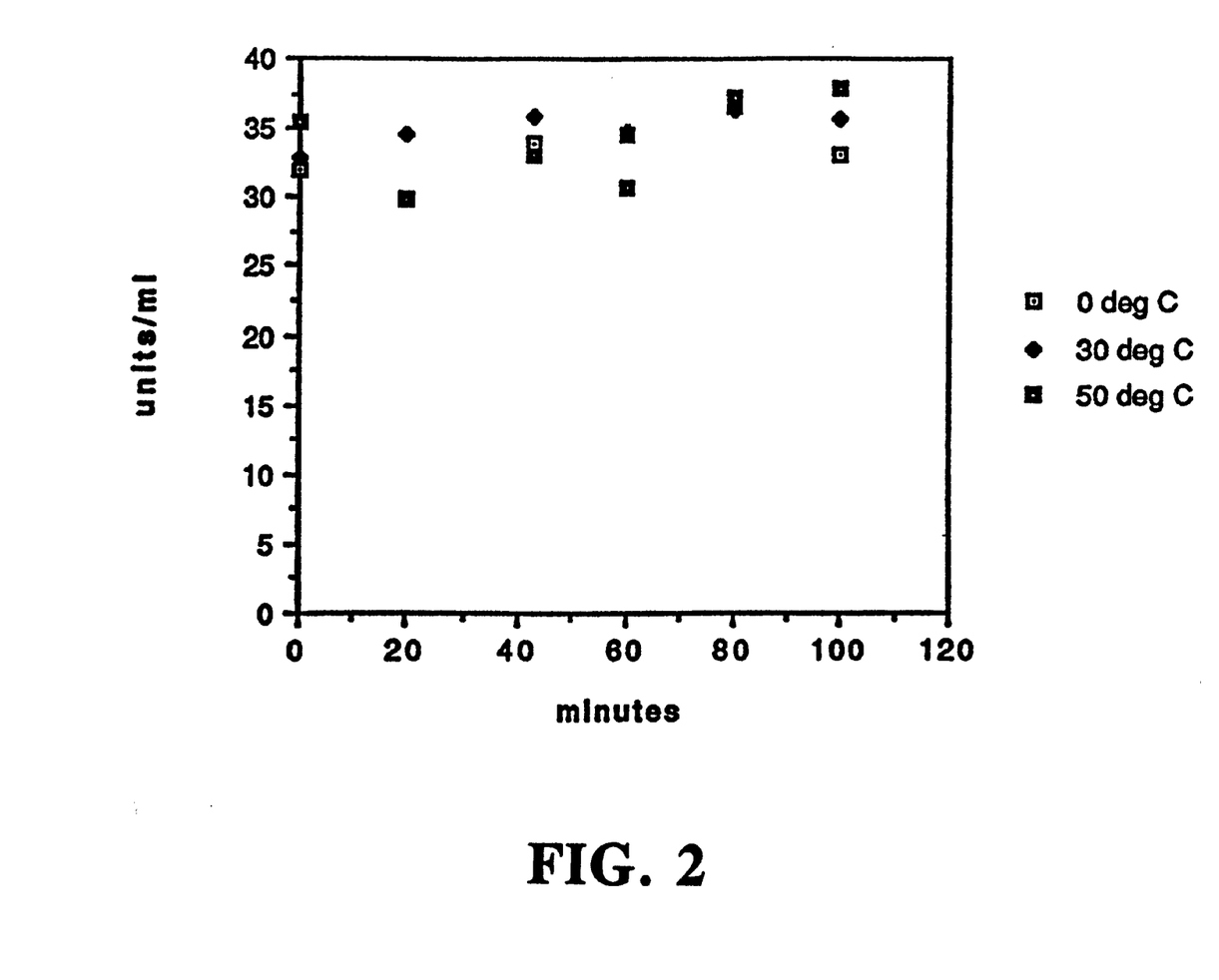
FIG. 2 is a graph depicting the temperature stability of phytase activity from the transgenic alfalfa described herein after treatment at 0° C. (empty squares), 30° C. (diamonds), and 50° C. (solid squares).

Fresh alfalfa juice from transgenic plants expressing phytase as described above were tested for phytase activity after treatment at 0° C., 30° C. and 50° C. over a period of 100 minutes. In all cases, phytase activity within the alfalfa juice was not detectably diminished after 100 minutes of incubation at the stated temperature. (See FIG. 2.) As shown in FIG. 2, the empty squares represent the samples treated at 0° C., the diamonds represent the samples treated at 30° C. and the solid squares represent the samples treated at 50° C.

Additionally, juice extracted from transgenic alfalfa and then concentrated retains approximately 88% of its initial phytase activity over a period of at least one month when stored at room temperature (about 22° C.).

The remarkable stability of the recombinant phytase enzyme from alfalfa makes the industrial application of this invention very attractive. Additionally, the fibrous material remaining after juice extraction also contains residual phytase. This residual phytase may also have feed value when fed to ruminants.

EXAMPLES

In order to more fully illustrate the present invention, the following Examples are provided. The Examples, which make reference to the attached Figures, are for illustration purposes only, to aid in a more complete understanding of the invention. The Examples do not limit the scope invention disclosed and claimed herein in any fashion.

Example 1

Expected Yields

This Example reports the expected yields of various alfalfa juice fractions, including phytase and xanthophylls, isolatable from transgenic alfalfa which constituitively expresses exogenous phytase originating from *A. niger*. Freshly expressed alfalfa juice was analyzed no less than 140 times on 40 days spanning a single growing season in Dane County, Wisconsin, extending from mid-June to mid-October. The results are presented in FIG. 1.

Figure 1:
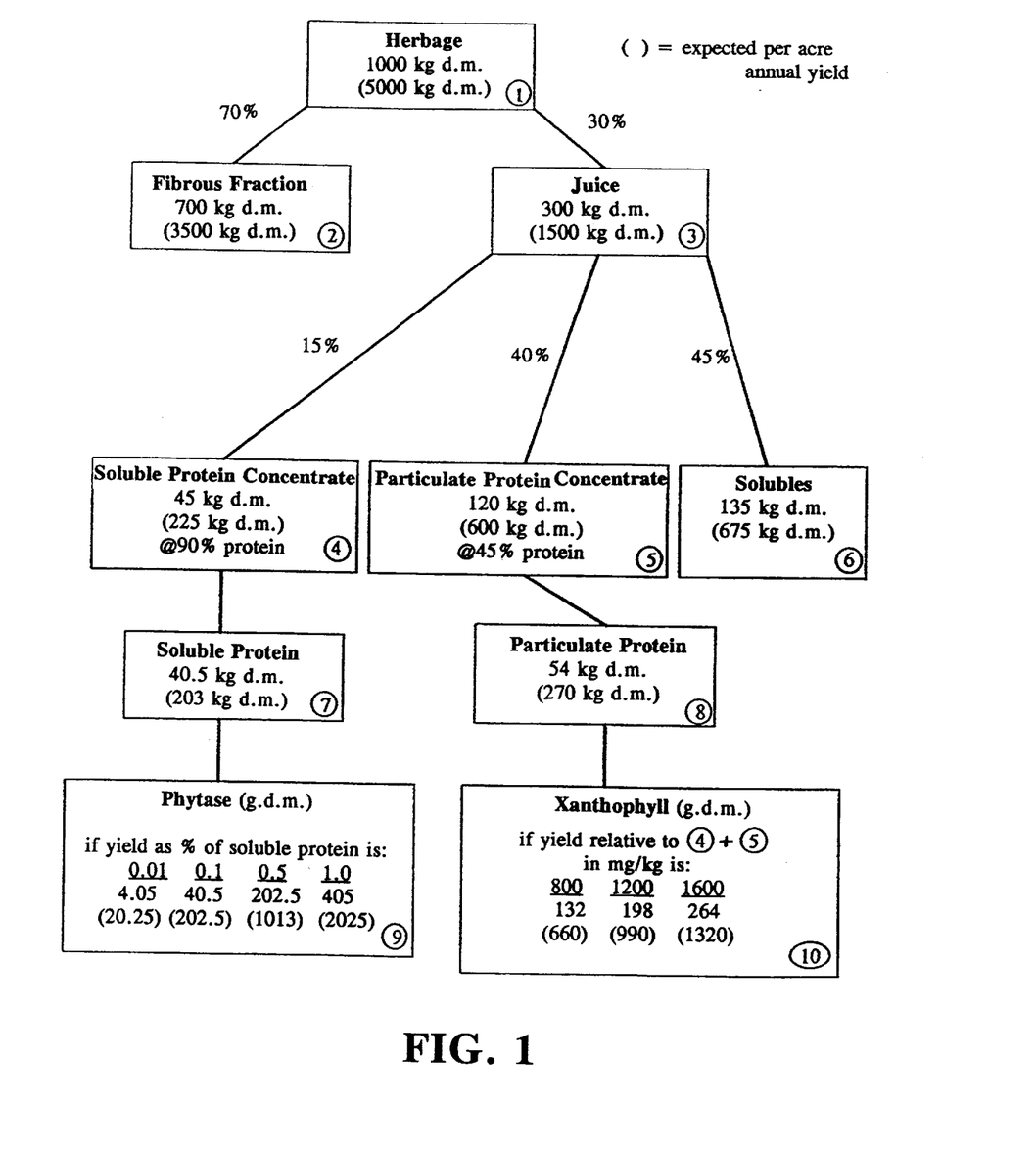
FIG. 1 depicts a flow chart describing the average yield of various products isolated from transgenic alfalfa which expresses phytase. The yields are listed on a per 1000 kilogram (kg) dry matter basis and, in parentheses, on a per acre expected annual yield basis.

Each box of FIG. 1 includes two designations. The first designation is the amount of the respective fraction based upon 1000 kg of harvested dry matter. The second designation is the amount of the respective fraction based upon an expected per acre annual yield. This designation is placed in parentheses ( ). This Example tabulates the complete isolation of soluble and particulate protein, phytase, and xanthophylls. Complete isolation of the individual components present in the transgenic alfalfa, as illustrated here, is not necessary to exploit the advantages of the transgenic alfalfa. This Example is solely to illustrate the relative amounts of soluble protein, particulate protein, phytase and xanthophylls which can be recovered from transgenic alfalfa.

As shown in boxes 2 and 3 of FIG. 1, each 1000 kg of dry matter (d.m.) after expression of the juice contained therein yields on average 700 kg of fibrous matter and 300 kg of juice, respectively. The fibrous matter can be used for any number of purposes, including as a feed for ruminants, a feedstock for biomass or ethanol production, a mulch, etc.

As depicted in box 4, the soluble protein fraction makes up approximately 15% by weight of the juice (dry matter basis), 90% of which is, on average, protein. Particulate proteins make up approximately 40% by weight of the juice, 45% (average) of which is protein (box 5), and 45% by weight of the juice dry matter is made up of other soluble components such as salts, sugars and the like (box 6).

Referring now to box 7, approximately 40.5 kg of soluble protein can be isolated per 1000 kg of dry herbage. Box 9 tabulates the amount of phytase which is contained within the soluble protein fraction as a function of the percent phytase present in the soluble protein fraction. For instance, if the soluble protein fraction contains 0.01 weight percent phytase, approximately 4.05 grams of phytase, on average, can be isolated from 1000 kg of dry herbage. If the soluble protein fraction contains 1.00 weight percent phytase, approximately 405 grams of phytase, on average, can be isolated from 1000 kg of dry herbage. The higher producing transformants described herein have had phytase yields greater than 1% of the soluble protein.

Boxes 9 and 10 detail the amount of particulate protein and xanthophylls which are found, on average, in alfalfa juice, respectively. As noted in box 10, the amount of xanthophylls present is calculated as a function of the total amount of soluble protein plus particulate protein concentrates isolated from the juice. The amount of xanthophylls recovered is directly proportional to the sum of soluble proteins plus particulate proteins. Consequently, as the amount of total protein increases, so does the amount of xanthophylls recovered.

Example 2

Non-ruminant Feed Supplement

Using the above average yields, the following conclusions can be drawn regarding the ability to supplement non-ruminant animal feeds with transgenic alfalfa which expresses exogenous phytase activity.

First, regarding phytase activity and the requirements of poultry and swine, the following requirements are generally accepted in the animal nutrition art:

1 unit phytase 1 μmole $PO_4$ released/min@pH 5.5 and 37° C.

Pure phytase=100 to 140 units per mg dry matter

Poultry require a minimum of 300 to 500 units phytase per kg ration, which corresponds to approximately 3.3 mg phytase per kg of ration, or 3.3 g phytase per metric ton of ration.

Swine require approximately 1000 to 1200 units phytase per kg ration, which corresponds to approximately 9.2 mg phytase per kg of ration, or 9.2 g phytase per metric ton of ration.

For this Example, poultry were considered to require 29 mg xanthophyll per kg ration, or 29 g xanthophyll per metric ton ration. Swine do not require xanthophyll.

The ratio of xanthophyll to phytase in poultry rations should preferably approximate a ration of 8.6:1 xanthophyll to phytase. This ratio is approximated when the xanthophyll yield is about 1,000 mg/kg of boxes 4 and 5 of the Figure (i.e. the fraction of soluble vs. particulate proteins isolated from the juice), and phytase is produced at the rate of approximately 0.5% of the soluble protein fraction (box 7 of FIG. 1).

At these rates, one acre of transgenic alfalfa produces enough phytase to supplement 30.4 metric tons of poultry feed. At a higher phytase yield of 0.5% phytase in the soluble protein fraction, the per acre yield of phytase is sufficient to supplement 304 metric tons of poultry feed.

Since swine rations require approximately 2.5 times the amount of phytase as compared to poultry rations, one acre of transgenic alfalfa yielding 0.5% phytase in the soluble protein fraction produces sufficient phytase to supplement 120 metric tons of swine ration.

It should also be noted that since swine do not require xanthophylls, there is economic potential to remove the xanthophylls (by partial fractionation or any other known means) present in the multi-component composition in the event that the composition is destined for swine feed.

Example 3
Storage Stability when Formulated into Poultry Feed

Figure 3:
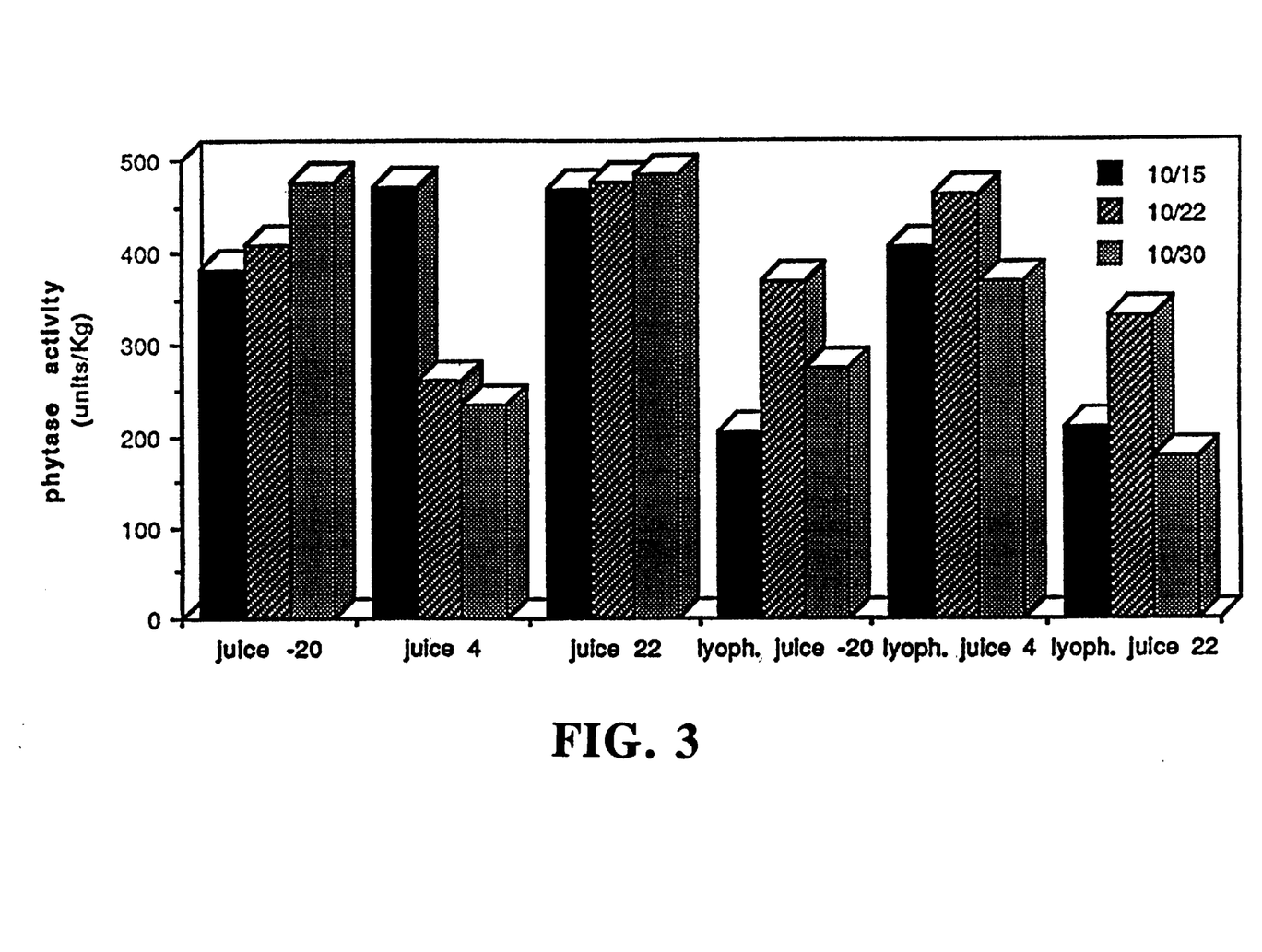
FIG. 3 is a graph depicting the phytase activity in basal poultry diets supplemented with frozen alfalfa juice from transgenic alfalfa ("juice") and concentrated juice from transgenic alfalfa ("lyoph. juice") expressing phytase after storage for 1, 2, and 3 weeks at −20° C., 4° C., and 22° C. (10/15, 10/22, and 10/30 correspond to week 1, week 2, and week 3 measurements, respectively.)

Both lyophilized and frozen whole alfalfa juice were used to supplement a standard poultry diet such that phytase activity of the feed was 400 units/Kg (1 unit=quantity of enzyme required to liberate 1 μmole inorganic phosphorus per minute from an excess of sodium phytate at 37° C., pH 5.5). Portions of treated feed were stored at 22° C., 4° C., and −20° C. After 1, 2 and 3 weeks of storage at these temperatures, representative samples were taken from each feed portion and assayed for phytase activity. The results of this Example are depicted in FIG. 3. As shown in FIG. 3, results for the feed portions supplemented with frozen alfalfa juice from transgenic alfalfa are designated "juice"; results for the feed portions supplemented with lyophilized juice from transgenic alfalfa are designated "lyoph. juice". The temperature under which each sample was stored is designated along the X-axis, and the Y-axis designates the phytase activity within each sample. The designations 10/15, 10/22, and 10/30 correspond to week 1, week 2, and week 3 measurements, respectively. No clear evidence of a loss in phytase activity over the 3 weeks of the experiment is evident.

The stability of transgenic phytase in poultry feed was also confirmed in the chicken feeding trials described below. During those trials, the phytase activity of feed samples removed and frozen on day 1 and day 11 was measured. Determined activities were 256 units/kg and 248 units/kg, respectively. Although the measured activities were lower than the expected 400 units/kg (possibly due to interference in the assay from feed constituents), no significant loss of activity was observed.

Example 4
Chicken Feeding Trials

In this Example, 6 populations of 25 chicks each were fed base diets which were either unsupplemented with inorganic phosphate, supplemented with various levels of inorganic phosphate, supplemented with whole juice from non-transformed alfalfa, or supplemented with whole juice from alfalfa transformed to express phytase as described above. The feeding trial continued for three weeks. At day 5 of the study, the populations fed unsupplemented rations or rations supplemented with non-transformed alfalfa juice displayed severe malnutrition and were euthanized.

The studies used one-day old male broilers obtained from Northern Hatcheries, Beaver Dam, Wisconsin. The broilers were vaccinated at day 1 against IBD and Mareks. The base diet from which all of the treatment diets were formulated was as follows:

Base Diet Formulation:

| Premix: | g/3 kg |
| --- | --- |
| Vitamin A (10,000 IU/g) | 135 |
| Vitamin D$_3$ (8900 IU/g) | 20 |
| Vitamin E | 27 |
| Riboflavin (100 g/lb) | 7.3 |
| Vitamin B$_{12}$ (300 mg/lb) | 3.6 |
| ZnSO$_4$ (36%) | 20 |
| MnO | 19 |
| Niacin (50%) | 22 |
| Pantothenic acid (25 %) | 28 |
| Choline (60%) | 287 |
| Bring to 3000 g with ground corn. | |

| Base Diet | kg/105 kg |
| --- | --- |
| Corn | 51.19 |
| Soybean Meal | 42.43 |
| CaCO$_3$ | 1.47 |
| Corn Oil | 7.23 |
| Methionine | 0.24 |
| Salt | 0.53 |
| Premix | 1.05 |

Treatment Diets:

The treatment diets, numbered 1 through 6, were formulated using the base diet as follows:

| | |
| --- | --- |
| 1. 0%† monocalcium phosphate | 570 g granite grit |
| 2. 33%† monocal. phos. | 188 g monocal and 382 g grit |
| 3. 66%† monocal phos. | 376 g monocal and 194 g grit |
| 4. 100%† monocal phos. | 570 g monocal |
| 5. Non-T* Juice | 410 g non-T juice + 160 g grit |
| 6. T** juice | 410 g T juice + 160 g grit |

†percent of NRC recommended allowance for monocalcium phosphate
*1.17 wt % juice from non-transformed alfalfa
**1.17 wt % juice from transformed alfalfa which expresses phytase Each treatment was added to 34.43 kg of feed from the base diet.

TABLE 1

Weight Gain in Chicks Fed Basal Diets Supplemented with Inorganic Phosphorous or Juice from Transgenic Alfalfa

| Diet % Added Mono-Cal-P | Added Juice | % Total Phosphorus | % Available Phosphorus | % Calcium | 0–2 week wt gain (g) |
| --- | --- | --- | --- | --- | --- |
| 1. 0 | 0 | 0.38 | 0.13 | 0.67 | Died @ d 5 |
| 2. 0.53 | 0 | 0.49 | 0.24 | 0.76 | 243 |
| 3. 1.06 | 0 | 0.61 | 0.36 | 0.85 | 272 |
| 4. 1.60 | 0 | 0.72 | 0.47 | 0.94 | 302 |
| 5. 0 | 1.17% Non-T* | 0.38 | 0.13 | 0.67 | Died @ d 5 |
| 6. 0 | 1.17% transformed** | 0.38 | 0.13 | 0.67 | 244 |

*1.17% juice from normal, non-transformed alfalfa
**1.17% juice from transgenic alfalfa expressing phytase activity Utilizing this data, a mathematical regression of % monocalcium phosphate added versus weight gain reveals that in this Example $R^2$=0.985 (weight gain in grams) and y 213.66+55.176 (% monocalcium phosphate). Therefore, based on equivalent weight gain, the juice from transgenic alfalfa increased the available phosphorous to the same extent as adding 0.55% monocalcium phosphate to the ration.

Week by week average weights and average weight gains for the 6 populations are reported in Table 2. Week by week feed-to-gain ratios, as well as the feed-to-gain ratios for the entire three-week study are presented in Table 3.

Example 5
Estimated Economic Impact on Chicken Production in the United States Replacing Supplemental Phosphate with Phytase Derived from Transgenic Alfalfa For this Example, the following estimates were employed:

- 6 billion broilers produced annually in the United States;
- average market weight equals 4 lbs. per broiler;
- 1.85 feed conversion ratio (1.85 lbs of feed/lb weight gain);
- average cost of supplemental phosphorous (monocalcium phosphate) equals $300/ton; and
- replacement value of phytase=0.55% added monocalcium phosphate.

Armed with the above assumptions, the annual economic value of phytase produced in transgenic alfalfa in the poultry industry in the United States is estimated as follows:

6 billion×4 lb.×1.85 lb. feed/gain÷2000 lb./ton×0.0055×$300/ton= value of phytase alfalfa juice=$36,630,000/year This number does not take into account to value of the xanthophyll and the dietary protein contained in the juice. In addition, the level of phytase in the ration was assumed to be 250 U/kg rather than the target 400 U/kg, suggesting that the juice might be used at almost double the level calculated above.

The estimated acreage required to produce 260,057 tons of alfalfa juice, the amount which would be needed in the above calculation, is 26,000 acres, which equals approximately 1% of the State of Wisconsin's alfalfa acreage.

If the juice concentration is doubled for poultry rations and increased 2.5 times for swine rations as compared to the poultry ration, the estimates calculted above would appear as follows:

Value of phytase alfalfa juice=$256 million

Amount of alfalfa juice required=1.82 million tons

Acreage required=182,000

% of Wisconsin alfalfa acreage 6%

Example 6
Pigment Content of Whole Alfalfa Juice

Frozen alfalfa juice from transgenic alfalfa (produced as described above) and non-transgenic alfalfa was analyzed for pigment content as described by Thayer & Björkman (1990). Average values of xanthophyll were 179 mg/kg whole juice (non-transformed control) and 123 mg/kg (transgenic alfalfa expressing phytase). These values correspond to approximately 1500 mg/kg and 1025 mg/kg juice dry matter, respectively (based upon 12% dry matter in juice).

Based on these values, xanthophyll pigment content of poultry feed contributed by non-transformed (control) alfalfa juice was 74 mg of pigment per 35 kg of feed and xanthophyll content of poultry feed contributed by transformed alfalfa juice was 50 mg pigment per 35 kg of feed. Previous work by others has shown that a level of approximately 1 gram of xanthophyll per 35 kg of feed is optimal for skin pigmentation in broilers. To achieve similar levels of xanthophyll using whole alfalfa juice would require adding approximately 800 grams of dried transgenic alfalfa juice per 35 kg of feed. Although this is more than the approximately 500 grams of inorganic phosphate which is normally added to the same quantity of feed, the alfalfa juice dry matter also contributes a significant quantity of protein. This indicates that the juice would partly replace the need to add other exogenous sources of xanthophyll to the ration.

Example 7
Stability of Transgenic Phytase in dried Plant Material

Experiments using transgenic tobacco expressing phytase showed that approximately 30% of the enzyme can be recovered from dried leaf material by simply grinding and rehydrating the leaves. The recovered activity has the same relative activity at high temperature and low pH, indicating that drying does not adversely affect the enzyme. Phytase expressed in alfalfa behaves in the same fashion.

It is understood that the invention is not confined to the particular methodologies herein illustrated and described,

TABLE 2

Average weight gains

| Diet | Avg. Wt. Day 1 | Avg. Wt. Week 1 | 0–1 Week Wt. Gain | Avg. Wt. Week 2 | 0–2 Week Wt. Gain | 1–2 Week Wt. Gain | Avg. Wt. Week 3 | 0–3 Week Wt. Gain | 2–3 Week Wt. Gain |
|---|---|---|---|---|---|---|---|---|---|
| 1 | 43 | — | — | — | — | — | — | — | — |
| 2 | 40 | 123 | 83 | 285 | 245 | 162 | 569 | 504 | 271 |
| 3 | 41 | 122 | 81 | 309 | 268 | 184 | 647 | 604 | 323 |
| 4 | 43 | 130 | 87 | 350 | 304 | 211 | 640 | 597 | 314 |
| 5 | 44 | — | — | — | — | — | — | — | — |
| 6 | 40 | 126 | 86 | 284 | 244 | 158 | 530 | 492 | 246 |

TABLE 3

Feed conversion ratios (feed-to-weight gain ratios)

| Diet | Week 1 Feed/Grain | 1–2 Week Feed/Grain | 0–2 Week Feed/Grain | 2–3 Week Feed/Grain | 0–3 Week Feed/Grain |
|---|---|---|---|---|---|
| 1 | — | — | — | — | — |
| 2 | 1.167 | 1.469 | 1.365 | 1.546 | 1.495 |
| 3 | 1.340 | 1.227 | 1.244 | 1.481 | 1.345 |
| 4 | 1.374 | 1.372 | 1.357 | 1.598 | 1.515 |
| 5 | — | — | — | — | — |
| 6 | 1.336 | 1.722 | 1.560 | 1.271 | 1.431 | but embraces such modified forms thereof as come within the scope of the following claims.

BIBLIOGRAPHY

Austin et al. (1994), An overview of a feasibility study for the production of industrial enzymes in transgenic alfalfa, Annals N.Y. Acad. of Sci., (721): 234–242.

Austin et al. (1995), *Euphytica*, 00:1–13.

Comai et al. (1990), *Plant Mol. Biol.* 15:373–381.

Ehrlich et al. (1993), *Biochem. & Biophys. Res. Comm.,* 195(1): 53–57.

Gibson, D. M. and Ullah, A. B. J. (1990), *Inositol metabolism in plants,* Wiley-LISS, Inc., 77–82.

Han et al. (1995), Proceedings of the 1995 Cornell Nutrition Conference for Feed Manufacturers, Rochester, N.Y., pp. 149–152.

Hughes, G. P. and Eyles, D. E. (1952), *Extracted Herbage Leaf Protein for Poultry Feeding,* J. Agric. Sci (Cambridge), 43:136–143.

Thayer & Björkman (1990), *Photosynth.* Res. 23:331–343.

Verwoerd et al. (1995), *Plant Physiology,* 109:1199–1205.

What is claimed is:

1. An animal feed composition comprising leafy plant material from transgenic alfalfa plants which constituitively express exogenous phytase activity at a concentration of at least about 0.5% by weight of soluble protein present in the transgenic alfalfa.

2. The animal feed composition of claim 1, wherein the transgenic alfalfa expresses phytase at a concentration of from about 1.0% to about 2.0% by weight of soluble protein present in the transgenic alfalfa.

3. The animal feed composition of claim 1 which is a poultry feed composition.

4. The animal feed composition of claim 1 which is a swine feed composition.

5. The animal feed composition of claim 1 which is a ruminant feed composition.

6. The animal feed composition of claim 1 which is a fish feed composition.

7. The animal feed composition of claim 1, further comprising juice, frozen juice, concentrated juice, or leafy plant material from non-transgenic alfalfa plants.

8. A method of feeding monogastric livestock or poultry which reduces or eliminates the need for phosphorous supplementation of monogastric livestock or poultry rations comprising: feeding monogastric livestock an animal feed composition of claim 1.

9. A method of feeding monogastric livestock or poultry which reduces or eliminates the need for phosphorous supplementation of monogastric livestock rations comprising: feeding monogastric livestock or poultry an animal feed composition of claim 7.

* * * * *